United States Patent [19]

Lodder

[11] Patent Number: 5,121,338

[45] Date of Patent: * Jun. 9, 1992

[54] METHOD FOR DETECTING SUBPOPULATIONS IN SPECTRAL ANALYSIS

[75] Inventor: Robert A. Lodder, Lexington, Ky.

[73] Assignee: Indiana University Foundation, Bloomington, Ind.

[*] Notice: The portion of the term of this patent subsequent to Jan. 9, 2007 has been disclaimed.

[21] Appl. No.: 730,394

[22] Filed: Jul. 11, 1991

Related U.S. Application Data

[63] Continuation of Ser. No. 359,084, May 30, 1989, abandoned, which is a continuation-in-part of Ser. No. 166,233, Mar. 10, 1988, Pat. No. 4,893,253.

[51] Int. Cl.$^5$ .......................................... G01F 15/46
[52] U.S. Cl. .................................. 364/498; 364/554; 250/339
[58] Field of Search ................ 364/554, 552, 496–499, 364/413.01, 413.05, 525; 250/338.1, 338.5, 339–343; 356/30, 36, 319, 328, 334; 382/6

[56] References Cited

U.S. PATENT DOCUMENTS

| | | | |
|---|---|---|---|
| 4,286,327 | 8/1981 | Rosenthal et al. | 364/498 |
| 4,399,361 | 8/1983 | Zanzucchi et al. | 250/343 |
| 4,466,076 | 8/1984 | Rosenthal | 364/498 |
| 4,496,839 | 1/1985 | Bernstein et al. | 250/341 |
| 4,540,289 | 9/1985 | Landa et al. | 356/328 |
| 4,620,284 | 10/1986 | Schnell et al. | 364/498 |
| 4,633,087 | 12/1986 | Rosenthal et al. | 250/341 |
| 4,652,756 | 3/1987 | Ryan et al. | 250/343 |
| 4,692,620 | 9/1987 | Rosenthal | 250/343 |
| 4,742,228 | 5/1988 | Bischoff | 250/341 |
| 4,785,184 | 11/1988 | Bien et al. | 250/343 |
| 4,800,279 | 1/1989 | Hieftje et al. | 250/339 |
| 4,801,804 | 1/1989 | Rosenthal | 250/339 X |
| 4,835,708 | 5/1989 | Frans | 364/497 |

OTHER PUBLICATIONS

R. Lodder, "Solving the False Sample in Near-Infrared Reflectance Analysis", University Microfilms, 1988.
R. Lodder et al., "Detection of Capsule Tampering by Near-Infrared Reflectance Analysis", Anal. Chem., 59(15):1921–1930 (1987).
D. L. Wetzel, "Near-Infrared Reflectance Analysis, Sleeper Among Spectroscopic Techniques", Anal. Chem., 55(12):1165–1172 (1983).
B. W. Hadzija et al., "Simple Techniques to Detect and Identify Phentermine Adulteration", Forensic Sci. Int'l, 23:143–147 (1983).
B. Efron, "Nonparametric estimates of Standard Error: The Jacknife, the Bootstrap and Other Methods", Biometrika, 68 (3): 589–599 (1981).
H. L. Mark et al., "Qualitative Near-Infrared Reflectane Analysis Using Mahalanobis Distances", Anal. Chem., 57:1449–1456 (1985).
H. L. Mark, "Normalized Distances for Qualitative Near-Infrared Reflectance Analysis", Anal. Chem., 58: 379–384 (1986).
D. E. Honigs et al., "Number of Samples and Wavelengths Required for the Training Set in Near-Infrared Reflectance Spectroscopy", Appl. Spectr., 38(6): 844–847 (1984).
D. E. Honigs et al., "Near-Infrared Spectrophotometric Metods Development with a limited Number of Samples: Application to Carbonate in Geological Samples", Appl. Spect., 39(6): 1062–1065 (1985).
Robert A. Lodder, "Quantile BEAST Attacks the False-Sample Problem in Near-Infrared Reflectance Analysis", Unpublished Manuscript.
Robert A. Lodder, "Detection of Subpopulations in Near-Infrared Reflectance Analysis", Apr. 1988.

Primary Examiner—Joseph L. Dixon
Attorney, Agent, or Firm—Kirkland & Ellis

[57] ABSTRACT

A method for using spectral analysis to detect subpopulations is disclosed. According to this method, a training set of spectra of a first plurality of samples is obtained and a bootstrap distribution is formed. A test set of spectra of a second plurality of samples is then obtained and a second bootstrap distribution is formed. First and second univariate distributions are then formed from the bootstrap distributions. A quantile-quantile relationship of the training and test sets is then developed and a determination of whether the test set and training set are substantially identical is made. The plurality of test samples are thus used to calculate probability density contours inside a training-set spectral cluster and detect perturbations of those contours using a bootstrap procedure. False samples are detected as subclusters well inside the training set, and trace analyses using a very small number of wavelengths are facilitated.

13 Claims, 7 Drawing Sheets

METHOD FOR DETECTING SUBPOPULATIONS IN SPECTRAL ANALYSIS

This is a continuation of co-pending application Ser. No. 07/359,084 (now abandoned) filed on May 30, 1989 which is a continuation-in-part of U.S. Ser. No. 07/166,233 filed Mar. 10, 1988 now U.S. Pat. No. 4,893,253 which issued Jan. 9, 1990.

BACKGROUND

The present invention relates to noninvasive and nonde-structive methods for screening irregular or inhomogeneous samples using spectral analysis and a nonparametric clustering algorithm.

The uses of near-infrared spectrometry have increased rapidly since the introduction of multiple linear regression and other pattern-recognition techniques to near-IR spectral data analysis. Near-infrared diffuse reflectance spectrometry is a fast analytical method that typically uses the reflectance of a sample at several wavelengths to determine the sample's composition. The technique is heuristic in its approach and makes extensive use of computers. Through a computational modeling process, near-infrared reflectance analysis is able to correct automatically for background and sample-matrix interferences, making ordinarily difficult analyses seem routine.

A model or calibration equation is typically a linear combination of equations of the form:

$$\text{concentration } (A) = c_0 + \sum_{i=1}^{d} c_i R_i$$

where A is a sample component of interest, d is the number of wavelengths at which measurements are obtained, the $R_i$ are the sums of the sample-component signals observed at each of i wavelengths, and $c_i$ are weighting coefficients often determined by multiple linear regression. It will be appreciated that although the present application is framed in terms of near-infrared reflectance measurements, any observable, such as mass, density, magnetic behavior, radioactivity, etc., or other information may be considered a "wavelength" for use in a calibration equation.

The modeling process employs a "training set" of samples to "teach" the computer algorithm to recognize relationships between minute spectral features and the sample's composition. Of course, the training set must have been previously analyzed by some other reliable (reference) chemical procedure. Although assembling a training set and developing a new calibration can require considerable time, the speed of subsequent analysis has provided plenty of impetus for the growth of near-IR reflectance methods.

Quantitative analysis of mixtures in the near-IR region has proven to be a powerful method of examining routine samples (samples whose basic composition is known). Qualitative applications of near-IR spectrometry have also been increasing in popularity, with the bulk of these identifications being performed on pure compounds or mixtures of low variability (in terms of both the chemical and physical compositions of the sample). As a result of the reliance upon pattern-recognition procedures, however, both qualitative and quantitative analysis can be complicated by the false-sample problem.

The false-sample problem arises whenever a pattern-recognition method is presented with a sample unlike any the method has ever analyzed before. In the regression-based analysis of spectral data, the false-sample problem arises when a test sample must be analyzed whose composition is outside the domain of the set of training samples used to develop the calibration equation. For example, the false-sample problem can appear as a result of: (1) trace contamination of the test sample; and/or (2) gross substitution of one sample component (one that was present in the training samples) for another component (one that was not present in the training samples); and/or (3) instrumental drift or sampling difficulties: and/or (4) variation of a component concentration beyond the range of concentrations used in the training set.

In quantitative spectrometry, using multiple linear regression to develop a prediction equation, any amount of extraneous signal at the analytical wavelengths (regardless of its source) generates a corresponding change in the predicted value of the analyte. When complex mixtures of high are qualitatively identified using distance or direction metrics defined in an analytical wavelength space, the extraneous signals at the analytical wavelengths change the distance or direction values used for sample identification. In other words, false samples can give rise both to erroneous analyte-concentration determination and to sample misidentification without any indication of the error.

Qualitative analytical methods designed for the detection of false samples using their near infrared spectra for quantitative near-IR spectrometry are disclosed in the present inventor's co-pending patent applications. Those detection methods allow different calibration equations to be employed automatically in the analysis of different kinds of samples (provided training samples are available for each sample type). Even if false samples cannot be identified as belonging to any known training set, an operator can still be alerted to the fact that the false sample cannot be predicted by the current calibration equation: "bad" samples can thus be removed from a process. Alternatively, a number of the false samples can be identified, collected, and analyzed to produce a training set that describes the previously unknown sample type. To date, however, false-sample detection in qualitative near-IR spectrometry has been largely unexamined.

In accordance with the present invention, a method employing the Bootstrap Error-Adjusted Single-sample Technique is provided that enables false-sample detection in both quantitative and qualitative spectrometry even when the false samples are "close" to the training samples.

The BEAST is a clustering technique for exploring multivariate data distributions. The technique considers each analytical wavelength to be a spatial dimension, so that spectra recorded at d wavelengths are represented as single points in a d-dimensional hyperspace. The magnitude of the signal observed at each wavelength is represented by the translation of the spectral point along each axis from the origin. Spectra of similar compounds produce clusters of points in a region of hyperspace as a consequence of this representation. A confidence-limit surface can be placed on a training-set spectral cluster by the BEAST (usually at three standard deviations, or 3 SDs, from the center of the training set cluster), and test samples whose spectra project as points inside this surface are said to be of the same type as the training samples. Test-sample spectra that project outside the 3 SD surface ("false sample" spectra) are not classified as members of the training-sample set.

It has been found that the spectral clusters can vary significantly in shape and size due to variations in sample packings, particle-size distributions, component concentrations, and drift with time. These factors, when combined with discriminant analysis using simple distance metrics, produce a test in which a result that places a particular point inside a particular cluster does not necessarily mean that the point is actually a member of the cluster. Instead, the point may be a member of a new, slightly different cluster overlapping the first that may be due to factors like low-level contamination or instrumental drift.

Methods of discriminant analysis that use distance metrics include the BEAST and those employing Mahalanobis distances: there are two principal differences between those methods. The Mahalanobis metric has often been referred to as a "rubber yardstick" whose length in spectral hyperspace depends upon the orientation of the stick. The "stretch" of the Mahalanobis distance is symmetric (i.e., grasping the yardstick at both ends and pulling produces identical increases in the lengths of the upper and lower halves of the stick). The stretches of the upper and lower halves of the BEAST yardstick, as set forth in co-pending U.S. patent application Ser. No. 07/358,813, filed May 30, 1989, for Method for Analyzing Asymmetric Clusters in Spectral Analysis, are not necessarily equal and depend upon the skew of the training set in the direction of the yardstick. This is an important capability to have in a metric when subclusters exist in the training set, when the response in one or more spectral dimensions is nonlinear, etc. In addition, the BEAST is a simple algorithm whose basic operations are random shuffling, sorting, and distance measurement that are relatively easy to distribute among a number of processors. The advantages of the BEAST over Mahalanobis metrics generally result from the nonparametric (i.e, making few assumptions about the nature of the underlying data distribution) nature of the BEAST.

Particle-size variations, noise, drift, trace contamination, and other factors can all create a situation in which a simple discriminant test that places a single sample inside a training-set cluster does not necessarily indicate that the sample appropriately belongs to the training set. Instead, the sample can be member of a new, slightly different cluster that overlaps the training set. Many possible process problems could demonstrate this overlap effect; for example, a single intact capsule, prepared from a reagent container contaminated with floor sweepings, would likely pass a near-IR examination based upon ordinary discriminant analysis.

SUMMARY

In accordance with the present invention, there is provided a method for detecting subpopulations in spectral analysis comprising the steps of collecting collecting a training set of spectra of a first plurality of samples from a population: forming a first bootstrap distribution from the training set: collecting a test set of spectra of a second plurality of samples: forming a second bootstrap distribution from the test set; forming first and second univariate distributions from the first and second bootstrap distributions: calculating a quantile-quantile relationship of the training and test sets: and determining whether the test set was drawn from a population substantially identical to the population from which the training set was drawn based on the quantile-quantile relationship.

The plurality of test samples are thus used to calculate probability density contours inside a training-set spectral cluster and detect perturbations of those contours using a bootstrap procedure. False samples are detected as subclusters well inside the training set, and "trace" analyses and analyses using a very small number of wavelengths are facilitated.

BRIEF DESCRIPTION OF THE DRAWINGS

The various objects and advantages of the present invention will be better understood after a reading of the following detailed description in conjunction with the drawings in which.

DETAILED DESCRIPTION

Figure 1:
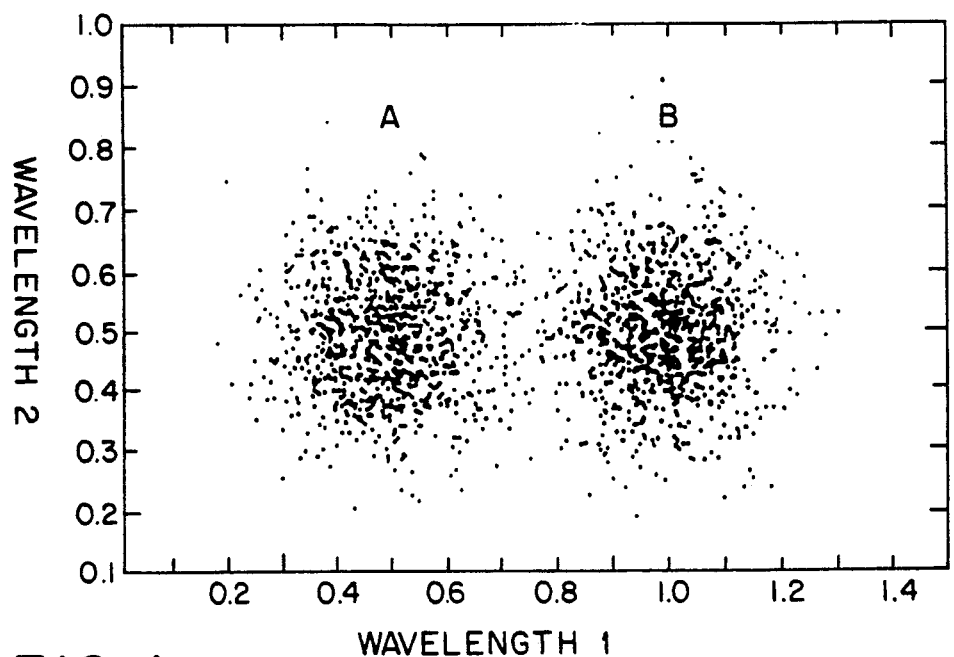
FIG. 1 shows two-thousand bootstrap-replicate spectra recorded at two wavelengths and projected as points in a two-dimensional space.

The BEAST is a flexible clustering procedure that is used in accordance with the present invention to search for subclusters within a training set by forming a training set T and a test set X and calculating those sets' respective bootstrap distributions B and $B_{(X)}$.

A training set of sample spectral values (e.g., reflectance, absorbance, etc.) recorded at d wavelengths from n training samples of a population is represented by the n-by-d matrix T. (Generally, another n-by-d matrix V of spectra from validation samples is also assembled from the same source as the training set. The validation sample set V serves as an indicator of how well the training set describes the overall population variation.) The training set is carefully constructed from known samples (samples that have been analyzed or identified by a suitable reference procedure) that adequately describe all possible sample variations. This step is common to many spectral analysis procedures. As described in more detail below, the test set X also comprises sample spectral values recorded at d wavelengths, and these results apply when the numbers of training and test samples are substantially equal. It will be appreciated that differing numbers of training and test samples are expected to yield good results with the present method by using a suitable transformation function to make the sizes of the training and test sets otherwise appear to be substantially equal.

A predetermined number m of bootstrap replications are calculated from T, X, and V, and the results are the bootstrap distributions, the m-by-d arrays B, $B_{(X)}$, and $B_{(V)}$. The calculation can be initiated by filling a matrix P with sample numbers to be used in bootstrap sample sets $B_{(s)}$:

$$P = p_{ij} = r$$

where r is a random number between zero and unity. The values in P are scaled to the training-set size by:

$$P = [n\, P + 1]$$

where the square brackets indicate the largest integer. A bootstrap sample set $B_{(s)}$ is then created for each row i of the m-by-d bootstrap distribution B by:

$$B_{(s)} = t_{Kj}$$

where K are the elements of the i-th rows of P and t are the elements of T. The q-th row of B is filled by the center of the q-th bootstrap sample set by:

$$b_{qj} = \sum_{i=1}^{n} b_{(s)ij}/n$$

and the center of the bootstrap distribution is $$c_j = \sum_{i=1}^{m} b_{ij}/m$$

The foregoing operations are then repeated using X and V. Thus, a randomly selected set of samples (containing the same number of elements as the training set T) is drawn from the training set, with replacement from the training set, to form a bootstrap distribution by Monte Carlo approximation. Bootstrap-replicate spectra recorded at two wavelengths of two hypothetical mixtures are shown projected as points in a two-dimensional hyperspace in FIG. 1. Each point represents the center of a bootstrap sample set: one thousand spectra form a cluster A, and one thousand spectra form a cluster B. It will be appreciated that a bootstrap distribution is used to estimate the true population distribution for a sample set.

In accordance with the present invention, the multivariate data in the bootstrap distributions are reduced to a univariate form by:

$$s_{(T)i} = \left( \sum_{j=1}^{d} b_{ij} - c_j)^2 \right)^{\frac{1}{2}}$$

$$s_{(X)i} = \left( \sum_{j=1}^{d} (b_{(X)ij} - c_j)^2 \right)^{\frac{1}{2}}$$

$$s_{(V)i} = \left( \sum_{j=1}^{d} (b_{(V)ij} - c_j)^2 \right)^{\frac{1}{2}}$$

and these distances are ordered and trimmed according to a trimming-index set given by:

$$P_{(T)} = \{mp+1, mp+2, mp+3, \ldots, m\text{-}m\}$$

It will be understood that the trimming index p is empirically selected to compensate for skew in the bootstrap distributions, i.e., to reduce the leverage effect on the center of isolated selections at the extremes of the bootstrap distributions.

As another way of compensating for skew, a hypercylinder can be formed about the line connecting C to the center of $B_{(X)}$ or $B_{(V)}$, giving directional selectivity to the information in $S_{(T)}$, $S_{(X)}$, and $S_{(V)}$ if desired. Each test-sample spectrum is projected into the same hyperspace as the bootstrap distribution, and a line is formed in hyperspace connecting the center of the bootstrap distribution and the test-sample spectral point. A hypercylinder formed about that hyperline contains a number $n_h$ of points from the bootstrap distribution. The coordinates of the points within the hypercylinder are transformed into distances from the center of the bootstrap distribution, and those distances are projected onto the hyperline at the center of the hypercylinder. The projected distances form a univariate distribution whose quantiles are used to construct confidence limits in the direction of the hyperline. The vectors $S_{(T)}$, $S_{(X)}$, and $S_{(V)}$ whose elements are shown above then have $n_h$ elements (preferably at least 50) instead of m elements. Subclusters can be detected without this selectivity, although directional selectivity adds to the sensitivity of the subcluster test. The details of the calculations relating to distance projection onto a hyperline are presented in co-pending U.S. patent application Ser. No. 07/358,813, filed May 30, 1989 cited above and incorporated herein by reference, now abandoned.

In accordance with the present invention, cumulative distribution functions (CDFs) for quantile-quantile plotting are formed by:

$$C_{(C)} = \partial(S_{(T)P(T)}, S_{(C)P(T)})$$

$$C_{(X)} = \partial(S_{(T)P(T)}, S_{(X)P(T)})$$

$$C_{(V)} = \partial(S_{(T)P(T)}, S_{(V)P(T)})$$

Figure 2:
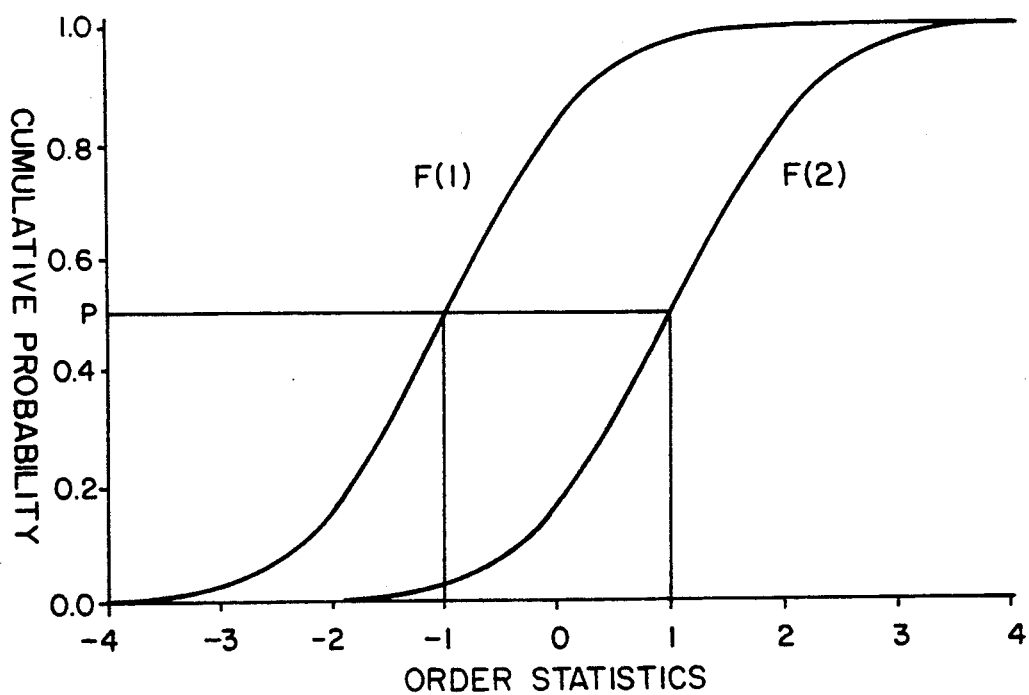
FIG. 2 shows cumulative distribution functions (CDFs) from spectra similar to those in FIG. 1

FIG. 2 shows CDFs from spectra similar to those in FIG. 1. The abscissa values in FIG. 2 are the normalized Euclidean distances of each point in FIG. 1 from the center (group mean) of training set A. CDFs F(1) and F(2) are typical of clusters that differ only in the locations of their centers in spectral hyperspace. As quantile level p is varied, the intersections of F(1) and F(2) with a horizontal line select pairs of CDF abscissa values that are used for quantile-quantile (QQ) plots. In FIG. 2 for example, the abscissa value of the point for the p-th quantile in the QQ plot of F(2) against F(1) would be −1, and the ordinate value would be +1.

In general, CDF plots such as FIG. 2 test the location, shape, and scale of an empirical distribution (ECDF), but to use such a plot to decide whether or not a given set of variables follows a specified CDF, the location and scale parameters of the distribution must first be estimated. This estimation process can range from being merely difficult to nearly impossible. In many cases, neither a conventional chi-square method nor a simple CDF comparison method provides a satisfactory solution to the distribution-analysis problem.

Another problem with simple CDF plots is that they often fail to reveal significant variations in curves near $p=0$ and $p=1$ —regions which are often of critical concern. For instance, when one investigates whether an ECDF is normal, the outliers are of major importance. If outliers contaminate 10% of the data, then the regions between zero and the fifth percentile and between the ninety-fifth and one hundredth percentiles are of great interest. A plot that decompresses the data in these regions possesses the greatest utility.

QQ plots do not suffer from these data-compression and parameter-estimation problems. By obtaining quantiles from CDF plots and plotting them versus each other (e.g., $F^{-1}(2)(p)$ on the y-axis and $F^{-1}(1)(p)$ on the x-axis) those difficulties are avoided. The notation $F^{-1}(p)$ indicates the empirical inverse of the cumulative distribution function given by the order statistics.

It will be understood that the probability plotting positions (p) are not chosen randomly to give quantiles for plotting; equations are known that give the best positions for families of cumulative distribution functions. See S. W. Looney and T. R. Gulledge, J. Statist. Comput. Simul. vol. 20, pp. 115–127 (1984). The fact that ECDFs are discrete makes them necessarily somewhat ambiguous. As a result, sampled ECDF points for simplicity are composed of elements of the set of order statistics (the rank-ordered, n experimental data points.) The corresponding points of the theoretical CDF (TCDF) are $F^{-1}(p)$ where $p=(i-0.5)/n$ or some other cumulative probability position, such as $p=(i-0.4)/(n+0.2)$.

This quantile-selection procedure yields a straight line with unit slope through the origin if F(1) is identical to F(2) because if two functions (f(1) and f(2)) of x are identical, a plot of their integrals (F(1) and F(2)) from negative-infinity to x, as x is allowed to vary through the domains of the functions, produces two identical vectors of points (F(1),i and F(2),i). Plotting F(1),i versus F(2),i gives a straight line. If F(1) differs from F(2) by only a location and/or scale change, the plot will still be a straight line, but with a slope and intercept that depend upon the values of the location ($\mu$) and scale ($\delta$) changes. (Note that location and scale changes are normalized for comparisons between CDFs by a simple relationship: if $F(2)(x)=F(1)((x-\mu)/\delta)$, the slope of the line formed will be $\delta$ and the intercept will be $\mu/\delta$.) If F(1) differs from F(2) in a more fundamental way, the QQ plot will no longer be a straight line.

Plotting the elements of $C_{(T)}$ on the abscissa versus the elements of either $C_{(X)}$ or $C_{(V)}$ on the ordinate produces a standard QQ plot. In accordance with the present invention, patterns in such plots and the significance of the correlation between $C_{(T)}$ and $C_{(X)}$ are used to analyze structure in the spectral data and to indicate the existence of subclusters in the spectral data. In the QQ plot as described above, a straight line with unit slope and zero intercept indicates that the two cumulative distribution functions are essentially identical (this should be observed when $C_{(V)}$ is on the ordinate, being compared to $C_{(T)}$). The presence of breaks or bends in the line in the QQ plot indicates that the CDF on the ordinate is multimodal, i.e., that the test set and training set of samples are not the same.

Figure 3:
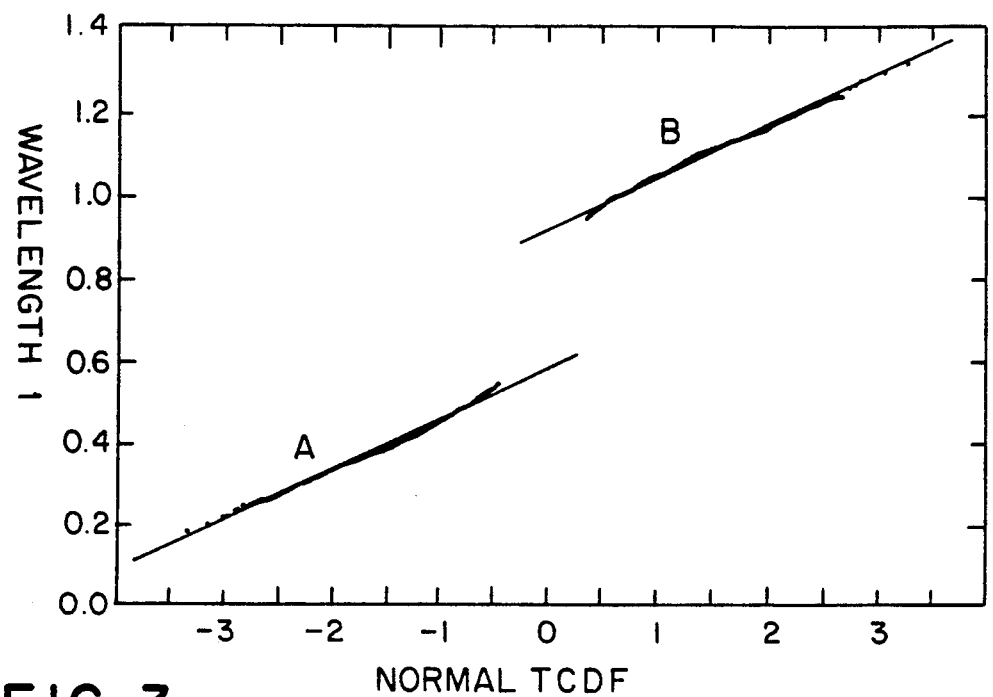
FIG. 3 shows a QQ plot of a bimodal distribution.

FIG. 3 shows a QQ plot of a bimodal distribution such as that of FIG. 1, with a normal cumulative distribution function on the abscissa and one wavelength along the ordinate. The slopes and intercepts of the line segments in the Figure are determined by suitable conventional linear fitting methods such as ordinary least squares regression, and the conventional product-moment correlation coefficients are measures of the goodness of fit of the fitted line to the data.

EXAMPLES

Equipment.

Spectral data for the following examples were collected using a Technicon Instruments Corp. INFRA-ALYZER 400 filter spectrophotometer. The spectrophotometer was directly connected to a VAX 11/780 computer (Digital Equipment Corp.), and spectral data were recorded at 18 wavelengths. The present method was implemented in the easy Computing Corp., Chicago, Ill.). Intact pharmaceutical capsules used as samples were individually scanned using a 90° conical aluminum holder/reflector which is the subject of co-pending U.S. patent application Ser. No. 07/165,751.

Materials.

Samples were prepared from MAXIMUM STRENGTH ANACIN-3 acetaminophen capsules (500 mg acetaminophen, Whitehall Laboratories, Inc., New York). These capsules have a blue end (cap) and a white end (body). In the contamination examples below, the training samples were unadulterated ANACIN-3 acetaminophen capsules, but they were emptied and repacked so that sample variations introduced by the repacking process appeared uniformly in the training, validation, and test sample sets. The validation samples were likewise unadulterated, repacked ANACIN-3 acetaminophen capsules. Several training and validation sets were prepared, each containing 10–13 capsules.

Consider the following hypothetical process problem: a small plant, perhaps a pharmaceutical facility, receives raw materials in large drums and also removes its waste materials and garbage in somewhat similar drums. Naturally, the drums are color-coded and labeled. But suppose one night a new employee is sweeping the plant and, having filled his dustpan, inadvertently empties it into the wrong container. The next day, that cubic meter of reagent is used to produce pharmaceutical capsules.

Adulterants in the test-sample capsules were selected to simulate such a process-control problem. The first adulterant was aluminum dust (finest powder, Fisher Scientific Co., Fairlawn, N.J.). The aluminum powder was blown into empty capsules, and the amount that adhered to the capsule walls was measured by weighing each capsule before and after the addition of the dust. The second adulterant was ordinary dust: floor sweepings were obtained from the dry bag of a wet/dry vacuum cleaner. A sizable amount of this dust consisted of fibers (probably both natural and synthetic). The material was introduced into the capsules by emptying a number of test capsules into a beaker, mixing the material into the powder in the beaker, and repacking the capsules. By measuring the total weights of the analgesic powder and the floor sweepings, the average weight of floor sweeping per capsule was determined.

Types of Examples Performed

As a preliminary, bootstrap samples were drawn from a 13-sample validation set and analyzed with the present method to determine the adequacy of a training set composed of 13 intact ANACIN-3 acetaminophen capsules. The standard deviation of the product-moment correlation coefficients calculated from the 26 samples was 0.01, and the mean correlation coefficient was 0.99, indicating the training and validation sets were drawn from the same sample population. Thus, the training set adequately captured the variation of that population.

Once a validated training set was available, the first example sought to determine the effects of test sets with different locations and scales on the QQ plot and to ascertain the correlation coefficients returned by the present method. Preparing contaminated-capsules test sets that project at a precise location and scale in hyperspace is nearly impossible, so the test sets were created by computer manipulation of the location and scale of the ANACIN-3 acetaminophen training set. Normally distributed pseudorandom numbers were generated, relocated, and scaled to have the desired relationship to the ANACIN-3 acetaminophen training set. In each case examined, the test set and training set each contained 13 samples.

Three types of relationships between the training and test sets were characterized in this manner:

1. pure location differences between the training set and test set. A test set was created of the same scale as the training set in spectral hyperspace. As the hyperspatial centers of the sets were moved apart, the effects on the QQ plot and the correlation coefficient calculated from the plot were monitored.
2. pure scale or size differences between the training set and the test set a test set. A test set was created having the same center location as the training set in hyperspace. Again, as the hyperspatial sizes of the sets were varied relative to each other, the effects on the QQ plot and the correlation coefficient were monitored.
3. simultaneous differences in location and scale.

The second example determined the bias and relative standard deviation, RSD, for the present subcluster-detection procedure as a function of the number of training samples used, the number of bootstrap replications employed, the number of wavelengths monitored, and the radius of the hypercylinder. The second example used computer-generated data for both the training and test sets that each had the same number of samples. Normally distributed pseudorandom numbers were generated for both the training set and the test set for each comparison.

The third example examined real ANACIN-3 acetaminophen capsules produced with simulated process-control problems. The first problem was the contamination of test-set capsules with an average of 208 $\mu$g of aluminum dust per capsule ($\sigma = 136$ $\mu$g) for an average total capsule mass of 704 mg ($\sigma = 32$ mg). The second simulated process-control problem was the contamination of capsules with floor sweepings. A beaker containing 6.1052 g of analgesic powder from ANACIN-3 acetaminophen capsules was contaminated with 1.35 mg of floor sweepings. Ten capsules were packed with this material, giving an average concentration of 221 ppm floor sweepings in the capsules.

Results.

The results of the first example describe the behavior of the present subcluster-detection procedure as the location and scale of a test set of samples varies with respect to a fixed training set. Each of the location and scale tests in this example used the same fixed training set of 13 ANACIN-3 acetaminophen capsules and a different computer-generated set of test samples. As discussed above, the shape of the spectral data sets in hyperspace is not important to the present subcluster-detection procedure. In the example, the centers of the training and test sets were 0, 0.25, 0.5, 1, 1.25, 1.875, 2.5, 5, and 10 SDs apart. (The distance in SDs refers to the SD of either the training set or the test set. The fact that the two sets are of the same scale and the fact that each set was drawn from a population that was spheroidal in shape means that the SD of either set can be used in measuring the distance between the two set centers.)

Figure 4:
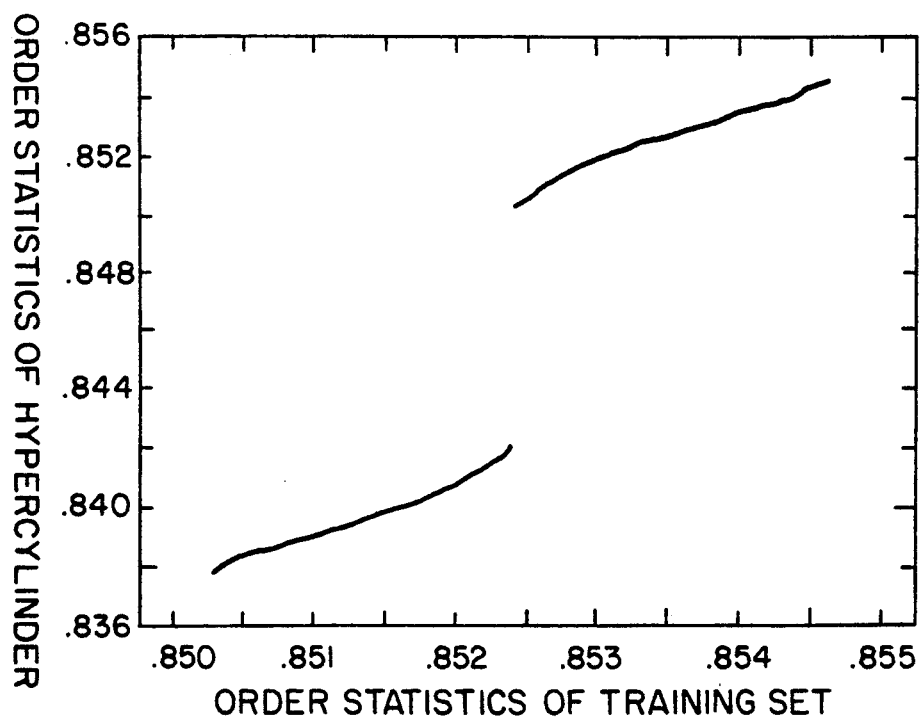
FIG. 4 shows a QQ plot from the subcluster-detection method corresponding to a pure location-difference situation.

The effect on the QQ plot of a pure location difference between the test set and the training set, i.e., the presence of a distinct subcluster in the training set, causes a break in the line of the QQ plot as shown in FIG. 4. The test set forms the lower line segment and the training set forms the upper line segment. (The ordinate contains data from the test set and the training set, while the abscissa contains only data from the training set. Thus, the axis range of the abscissa gives the range of the training set, which can then be compared to the values along the ordinate to determine which group is the training set and which group is the test set. In FIG. 4, the centers of the test-set and training-set distributions are 2.5 SDs apart. As the distance between the two centers was increased beyond 2.5 SDs, the slopes of the upper and lower line segments were reduced, and the gap between their near ends increased. As the distance between the two centers wa reduced below 2.5 SDs, the slopes of both line segments increased, and the gap between the ends shrank. When the distance between the two centers was 0.5 SD or less, no gap between the line segments was distinguishable: the test set behaved much like a validation set.

Figure 5:
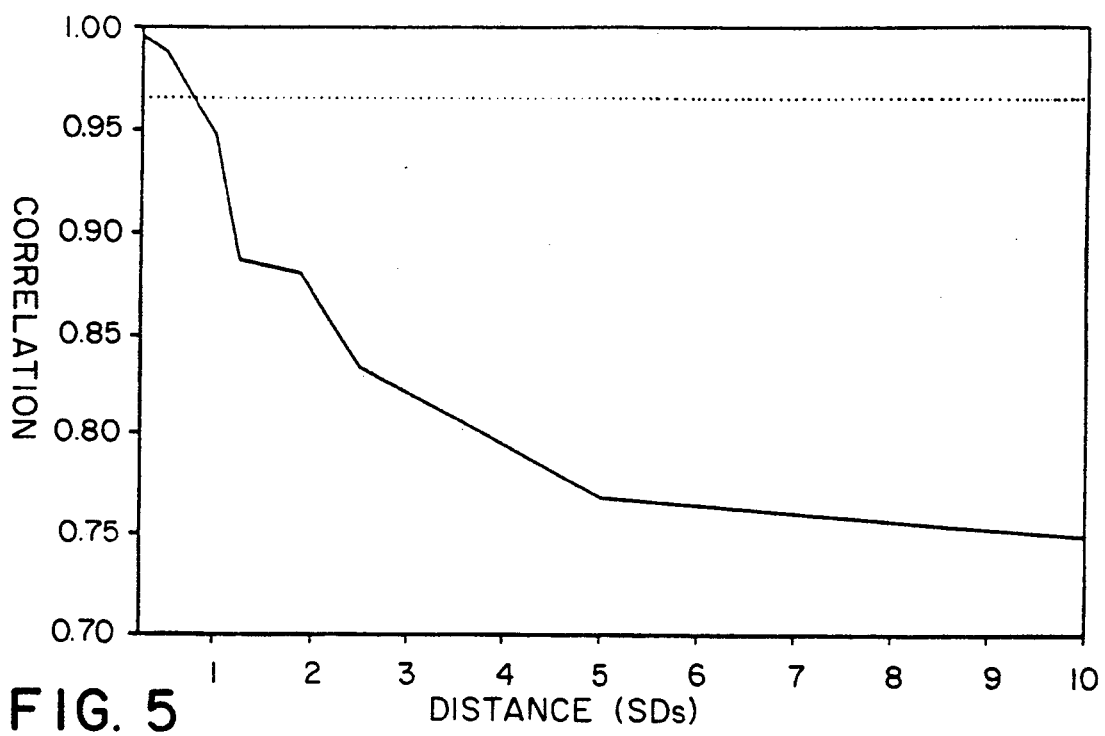
FIG. 5 shows the effect of a pure location difference on the correlation coefficient calculated from a QQ plot.

The effect of a pure location difference between the test set and the training set on the product-moment correlation coefficient calculated from the distributions in the QQ plot is shown in FIG. 5. The dotted line in the figure represents a lower confidence limit (2 SDs below the mean correlation coefficient, or the 98% level) calculated on the training set using validation samples. Above the dotted line, the training set and the test set would be indistinguishable, i.e., the test set would be said to be composed of the same type of samples as the training set. When the correlation coefficient is less than approximately 0.96, the test set is said to be different from the training set at the 98% level. It will be noted from FIG. 5 that when two otherwise equivalent sample groups were separated by more than approximately 0.8 SD, the present subcluster-detection procedure signalled the presence of a false-sample test set.

Scale differences between the test set and the training set also affect the QQ plot. It was found that the scale-difference effect depends upon weather the training set is larger than the test set, or vice versa. In both cases the scale-difference effect was investigated by creating test sets that shared the same center in hyperspace with the training set of ANACIN 3 acetaminophen capsules. The scale of the computer-generated test set was then expanded or contracted, and the effect on the QQ plot and correlation coefficient produced in accordance with the present subcluster-detection procedure was analyzed.

Figure 6:
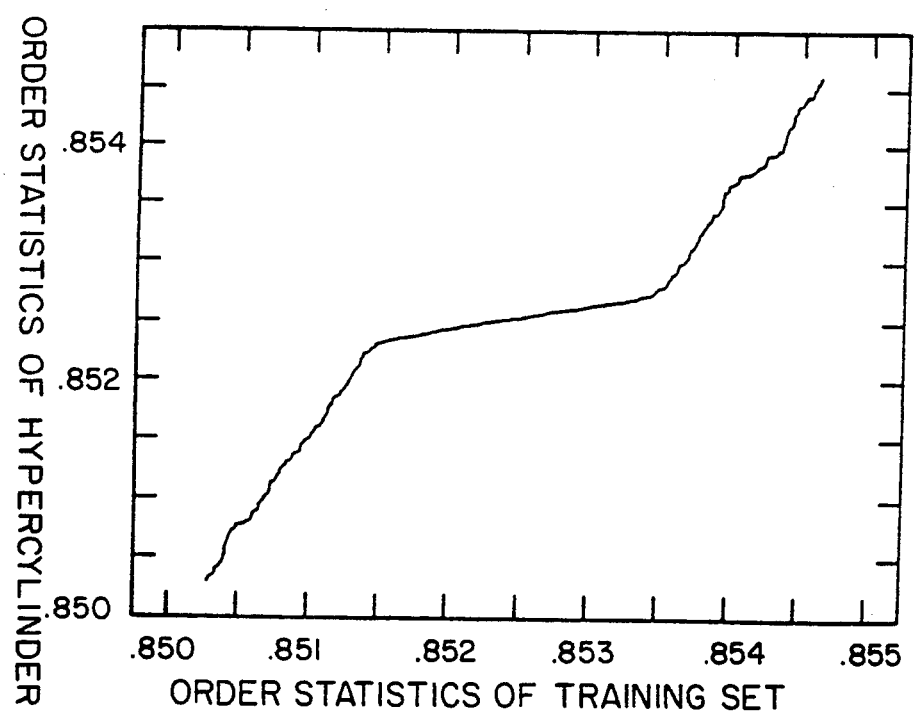
FIG. 6 shows a QQ plot from the present subcluster-detection method corresponding to a pure scale-difference situation.

FIG. 6 shows a QQ plot generated with a test set that was a factor of 5 smaller than the training set. The presence of a distinct subcluster in the spectral data on the ordinate causes the two sharp bends in the plot: the center line segment in the QQ plot is generated by the test set which separates the two end segments that correspond to the training set. As the test set grows larger, the slope of the center line segment increases and the two "bends" begin to disappear. When the test set is 1.25 times smaller than the training set, the slope of the center line increases to the point where it is difficult to tell if the center line segment is real.

Figure 7A:
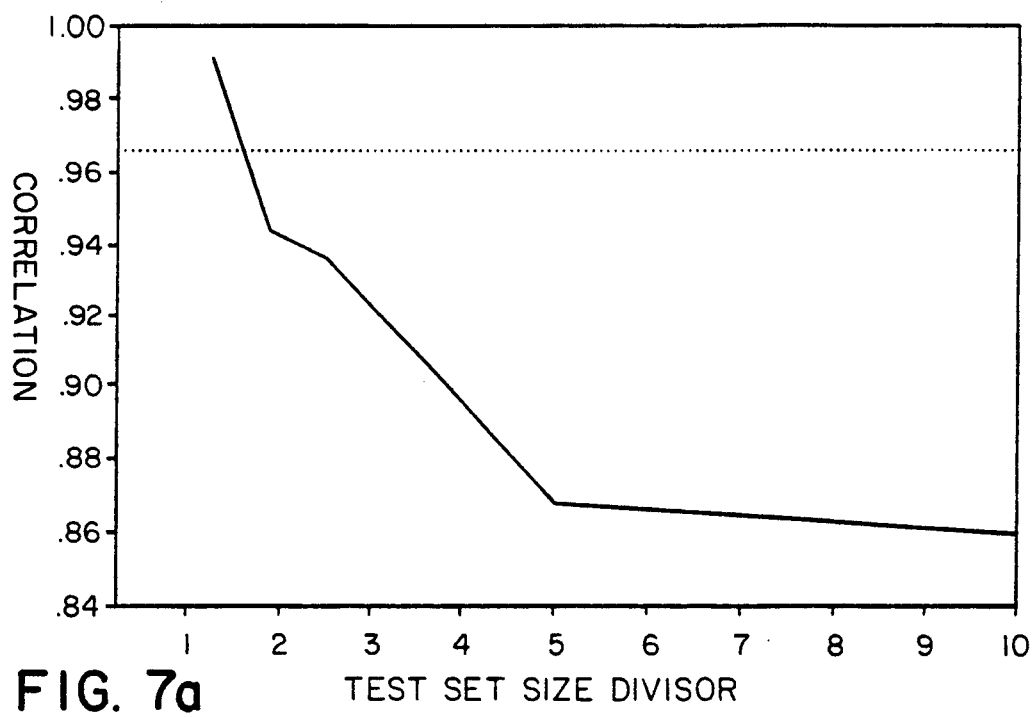
FIG. 7a shows the effect of a pure scale difference (test set smaller than the training set) on the correlation coefficient calculated from a QQ plot.

FIG. 7a describes the effect of scale difference when the training set is larger than the test set on the correlation coefficient calculated on the training set using validation samples. The dotted line shows the 98% confidence level, and the abscissa values are the factor by which the test set size is smaller than the training set size. When the test set is more than a factor of approximately 1.5 times smaller than the training set, the test set is flagged as a false-sample set even though the two sets share exactly the same center in hyperspace.

Figure 7B:
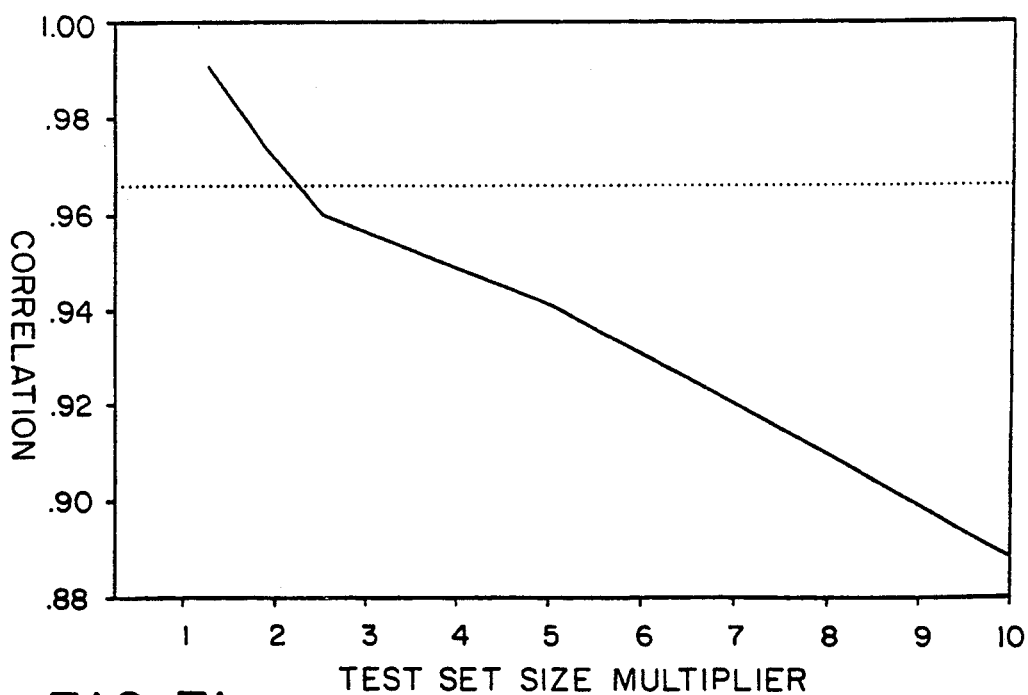
FIG. 7b shows the effect of a pure scale difference (training set smaller than the test set) on the correlation coefficient calculated from a QQ plot.

When the test set is larger than the training set in scale, a line segment with small slope also appears in the QQ plot, but it corresponds to the training set and appears at one end of the plot instead of in the center. This behavior reduces the sensitivity of the QQ plot and the correlation coefficient to changes in test-set scale. As shown in FIG. 7b, when the difference in scales is less than a factor of approximately 2.25 and the test set and training set share the same center, the test set appears to belong to the training-set population. The 98% confidence level is shown by the dotted line, and the abscissa values are the factor by which the test set size is larger than the training set size.

To get useful information from a single correlation coefficient calculated in the present subcluster-detection procedure, the relationship between the test-set and the training-set scales should be determined from the coefficients of the best-fit straight line through the QQ plot. It will be understood that the slope of the line contains information about the variance or spread of the data, and the intercept of the line contains information about the mean of the data. In a subcluster-detection situation (i.e., spectral data appearing near or within the 3 SD confidence limit of a training set cluster) when the test set is smaller than the training set, the slope of the best-fit line through the QQ plot will be between zero and unity. When the test set is larger than the training set, larger slopes (greater than unity) will be observed. It should be noted that large distances (more than 3 SDs) between the test-set and training-set centers also produce large slopes in the best-fit line on the QQ plot, but such distances do not represent false samples that would appear as training-set subclusters.

Figure 8:
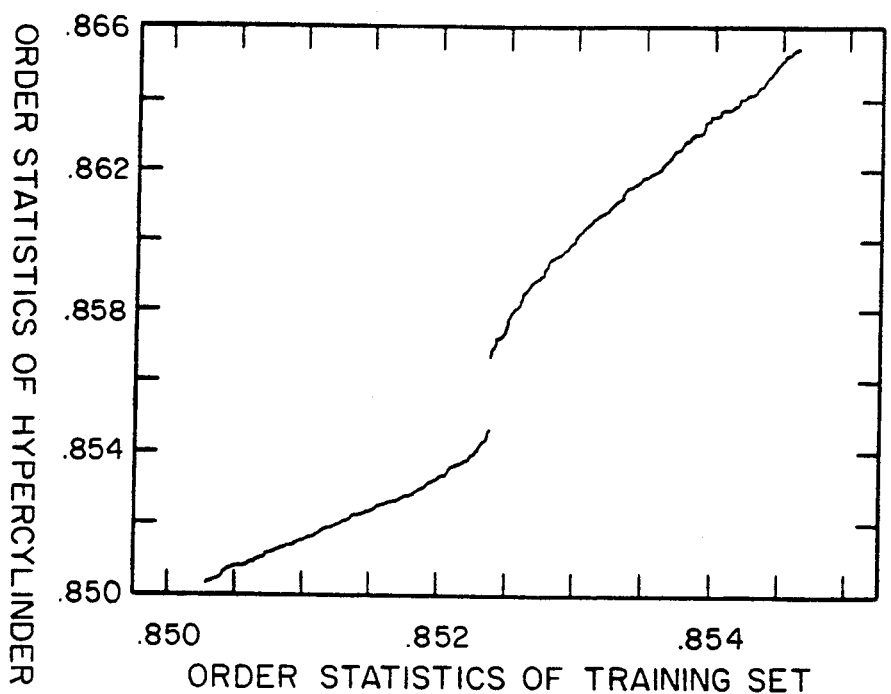
FIG. 8 shows a QQ plot from the present subcluster-detection method for simultaneous location and scale differences.

In most applications of the present subcluster-detection method, simultaneous differences in the location and scale of the test set would be expected in a false-sample situation. FIG. 8 shows a QQ plot for a computer- generated test set that was a factor of two larger in scale than the ANACIN-3 acetaminophen training set; the center of the test set and the training set were also 0.5 SD apart (measured using the smaller SD of the training set). The test set forms the upper line segment and the training set forms the lower line segment. Despite the small differences in the scale and location of the two groups, a clear break in the QQ plot is evident, indicating that a false-sample situation exists. As the test set becomes larger, the slope of the upper line segment increases. As the distance between the test set and training set increases, the size of the gap between the line segments also increases. The location-difference effect and the scale difference effect act in concert to make the present subcluster-detection method sensitive to very small differences between the spectral clusters. Even when, as shown, the two clusters differ in size by a factor as small as 2, the QQ plot indicates the presence of a subcluster in the data on the ordinate regardless of the difference in the locations of the two groups' centers.

When the test set is smaller than the training set and the distance between the two set centers varies, the QQ plot is still reasonably easy to interpret. The QQ plot has an inverse sigmoidal shape composed of three line segments and appears similar to the plot in FIG. 6 where the test set is also smaller than the training set. The line segment with the smaller slope is still the test set, but that line segment does not occur in the center of the QQ plot. Instead, the center of the test set line segment "slides" with constant slope along the imaginary $y=x$ line that would exist if the test set and the training set were drawn from the same population. The combined effects of location and scale differences between the two sets makes the QQ plot quite sensitive to minor differences that indicate a false-sample situation. When the test set is smaller than the training set by a factor of 5 or 10, the false-sample nature of the test set is apparent in the QQ plot regardless of the distance separating the two set centers. When the test set is smaller than the training set by a factor as small as 2, the false-sample nature of the test set is still apparent until the distance separating the set centers is only 0.1 SD.

Figure 9B:
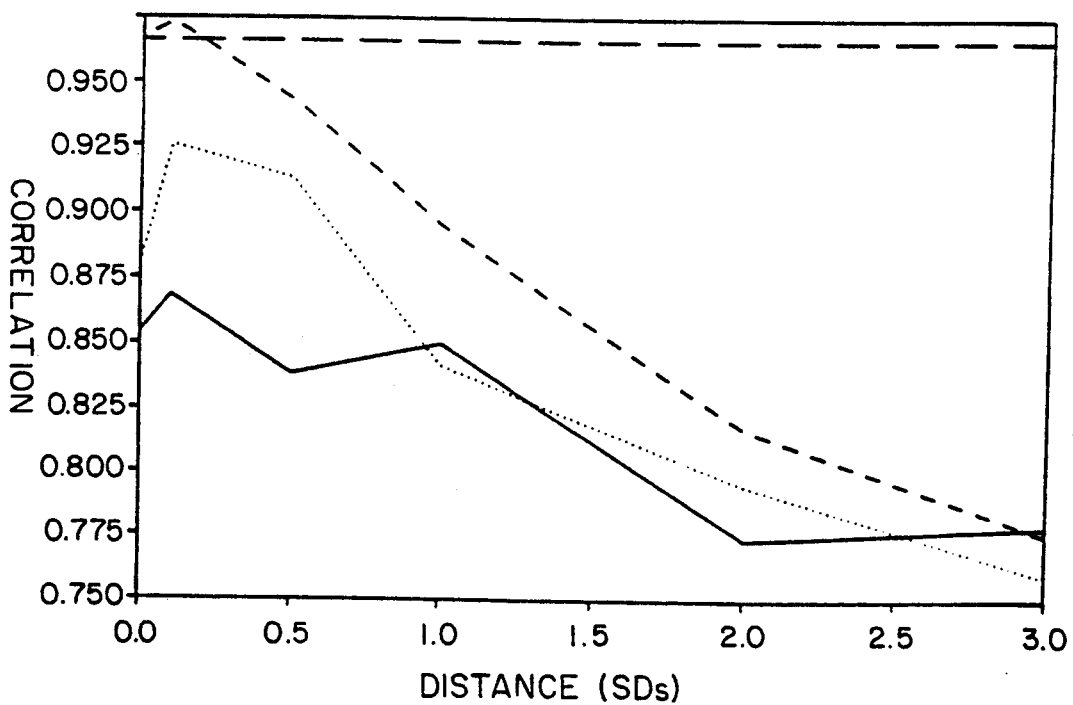
FIG. 9b shows the effect of simultaneous location and scale differences on the correlation coefficient calculated from a QQ plot when the test set is larger in scale than the training set.
Figure 9A:
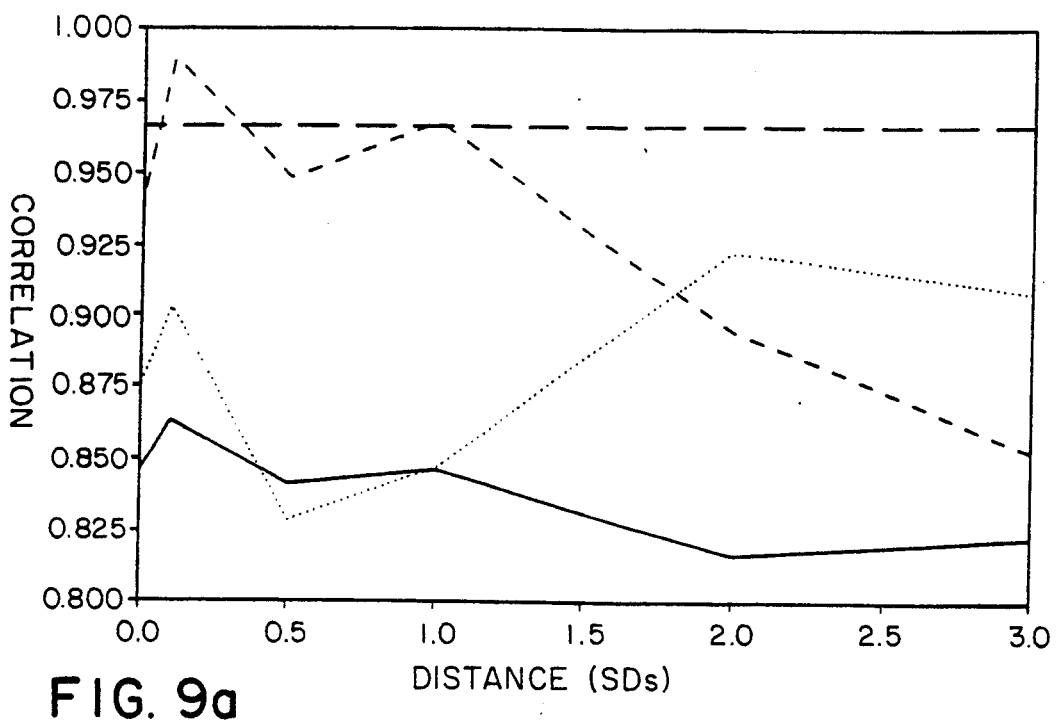
FIG. 9a shows the effect of simultaneous location and scale differences on the correlation coefficient calculated from a QQ plot when the training set is larger than the test set in scale.

Analyzing the behavior of the correlation coefficient when the test set is smaller than the training set and when the centers differ in location is more complicated than explaining the QQ plot appearance (see FIG. 9a). The abscissa values represent the distance between the two sets in SDs of the training set, and the horizontal long-dashed line represents a 98% confidence limit on the training set. The short-dashed line represents a training set that is a factor of 2 larger than the test set, the dotted line a training set that is a factor of 5 larger than the test set, and the solid line a training set that is a factor of 10 larger than the test set.

Two peaks appear in the graph of the correlation coefficient when the test set is smaller than the training set and the centers of the two sets are drawn apart. The first peak reflects a breakdown in the symmetry of the spectral sets in hyperspace and consequently in the QQ plot. At that point the correlation coefficient enters a "bend regime" where the difference between set scales dominates the correlation coefficient calculated from the QQ plot. As discussed above, the "bends" introduced by different set scales have a larger effect on the correlation when the bends occur in the middle of the line than when the bends occur at the end. After an initial drop in the correlation coefficient caused by its entering the bend regime, the correlation coefficient begins to rise again as the test set and training set continue to move apart. However, the difference in the locations of the set centers begins to exert an effect on the correlation coefficient. At that point the curves enter a "break regime", forming a second peak in the graph. In the break regime, the difference between the centers of the training set and test set dominates the correlation coefficient. Larger differences between the scale of the training set and test set cause later transitions into the break regime.

In FIG. 9a, the beginning of the bend regime becomes evident in each curve when the distance between the training set and test set centers reaches 0.1 SD. When the test set is a factor of 2 smaller than the training set (the short-dashed line), the break regime begins when the distance between the two set centers is around 1 SD. When the test set is a factor of 5 smaller than the training set (the dotted line), the break regime does not begin until the distance between the sets has reached 2 SDs. When the test set is a factor of 10 smaller than the training set (the solid line), the start of the break regime does not begin until the distance between the centers of the sets is beyond 3 SDs. It will be appreciated that despite the effects of the regime shifts, the present subcluster-detection method accurately flags as false samples test sets whose scales differ from the training set by a factor of 5 or 10 regardless of their distance from the center of the training set.

When the test set is larger than the training set (probably the more common real situation), the break regime occurs very early and dominates the curves (see FIG. 9b), and the regime-transition peaks overlap. Only when the training set is a factor of 10 smaller than the test set is the break regime transition peak delayed long enough to be resolved in FIG. 9b. It will be understood that the more alike the test set and training set are in terms of scale the larger the correlation is between them. A simple statistic such as the correlation coefficient is adequate for describing the behavior of the QQ plot when the test set is larger than the training set. The abscissa values represent the distance between the two sets in terms of SDs of the training set, and the horizontal long-dashed line represents a 98% confidence limit on the training set, and the short-dashed line represents a test set that is a factor of 2 larger than the training set, the dotted line a test set that is a factor of 5 larger than the training set, the solid line a test set that is a factor of 10 larger than the training set.

Bias and RSD of the Subcluster-Detection Procedure

The commonly adjustable experimental parameters, e.g., the number n of training samples (and test samples, as these were coupled in the present examples to simplify the testing procedure), the number m of bootstrap replications, the number d of wavelengths, and the radius $r_h$ of any hypercylinder, affect the bias and RSD of the correlation coefficient. Using computer-generated data for a training set and a test set that were both drawn from the same population (a nonfalse-sample situation that should produce a correlation coefficient of unity), bias and RSD plots for those four common experimental variables were created. Based on the plots, it will be appreciated that the training set should be well-distributed, and not assumed to be so merely because it was randomly selected.

Figure 10:
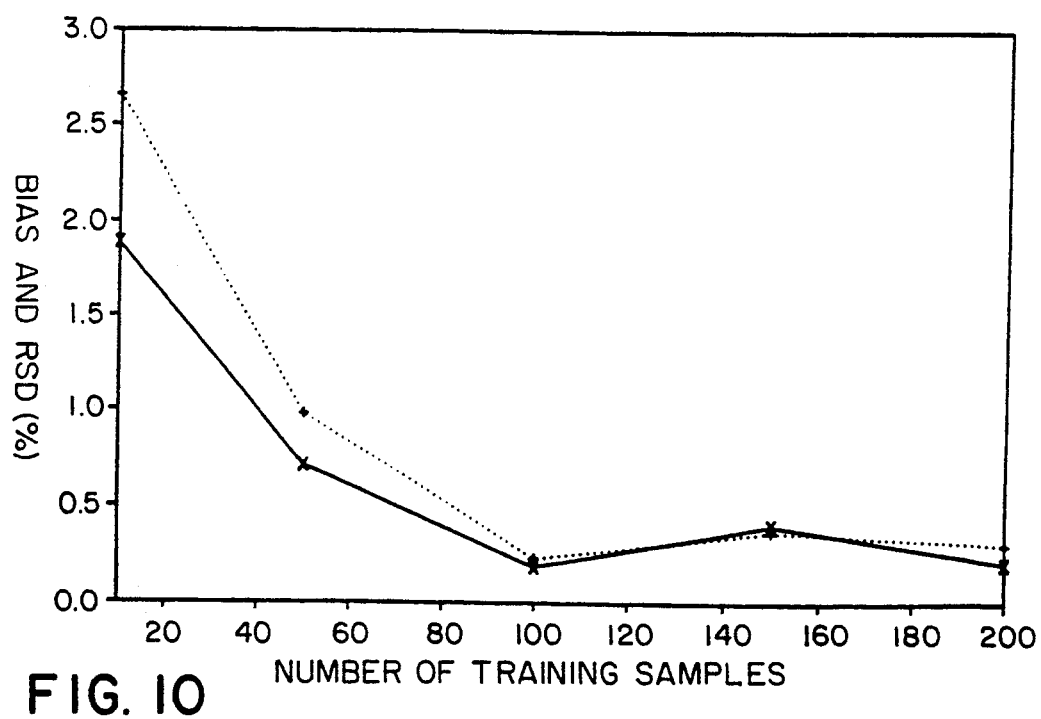
FIG. 10 shows the bias and RSD of the present subcluster-detection method's correlation coefficient as a function of the number of training (and test) samples for 2 wavelengths and 1000 bootstrap replications.

FIG. 10 shows the bias (dotted line) and RSD (solid line) of the correlation coefficient as a function of the number of training (and test) set samples. Each marked point comprises six trials using two wavelengths and 1000 bootstrap replications (no hypercylinder was used to screen out replicates in certain directions). The bias was the ratio of the difference of the known value and the value estimated by the present method to the known value. The RSD was converted from the mean-square error. Both the bias and the RSD decrease rapidly with an increasing number of samples, gradually reaching a plateau around 0.2–0.3% by the time 100 samples are used. The same plateau value was obtained in examining the effect of the number of bootstrap replications on the correlation coefficient.

The bias and RSD of the correlation coefficient were similarly examined as a function of the dimensionality of the hyperspace. It was found that as the number of dimensions increased, the hyperspace became sparsely populated with points, leading to a slow increase in the bias and RSD unless the number of spectral points was also increased. In other words, to describe more variables, more points are needed.

In addition, it was determined that the bias and RSD rose as the hypercylinder radius $r_h$, an important user-selected variable, was increased from zero (a theoretical hyperline). By the time the radius was increased enough to include all of the bootstrap replicate points, though, both the bias and the RSD dropped to approximately 0.2%. Such behavior is expected because the BEAST connects the mean or center point of a training set cluster in spectral hyperspace to a test spectral point with a hyperline. The univariate probability density along this hyperline is used to determine the probability that the test spectral point is actually a member of the population from which the training set was drawn. Since the probability density function is difficult to calculate, it is approximated by the finite number of points of the bootstrap distribution created from the training set. None of those points is likely to fall on the hyperline connecting the center of the training set and the test point. Accordingly, the hypercylinder is an approximation to the hyperline that works well in the single-sample case where the test statistic is the standard error in a specific direction. When the test statistic is the correlation coefficient between two clusters as in the present method, however, using a hypercylinder to exclude members of the groups makes the method sensitive to fortuitous agglomerations of points.

Pharmaceutical Capsules with Simulated Process-Control Problems.

A training set of ten repacked ANACIN-3 acetaminophen capsules and a validation set of ten repacked ANACIN-3 acetaminophen capsules were analyzed with the present subcluster-detection method. The QQ plot showed a continuous line having only two slight bends near the ends of the line. The correlation coefficient for the line was 0.995, well within the 90% confidence level of 0.966 calculated using 20 bootstrap sets derived from the validation samples.

Figure 11:
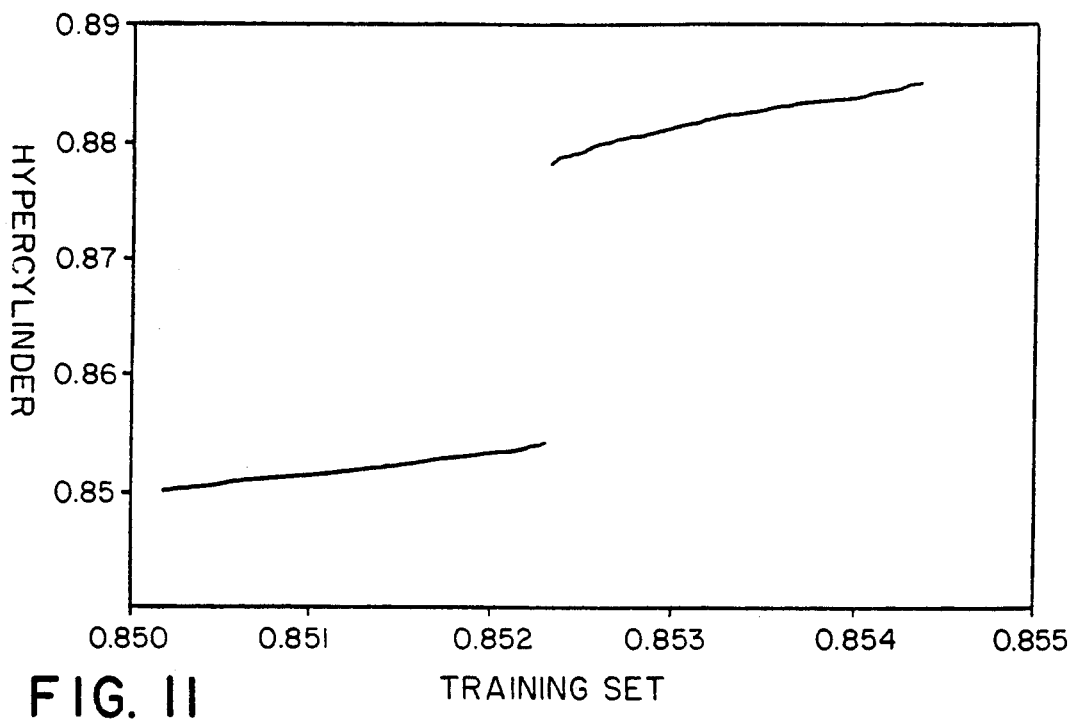
FIG. 11 shows a QQ plot from the present subcluster detection method created by ANACIN-3 acetaminophen capsules containing an average of 296 ppm aluminum dust and FIG. 12 shows a QQ plot from the present subcluster-detection method created by ANACIN-3 acetaminophen capsules containing an average of 221 ppm floor sweepings.

When aluminum dust was added to ten repacked ANACIN-3 acetaminophen capsules as described above, the present sub-cluster-detection method produced the QQ plot shown in FIG. 11. This plot has a correlation coefficient of 0.795, the lower line segment corresponding to the training set and the upper to the adulterated test set. The clear break indicates that the aluminum-containing test set was not drawn from the same population as the training-set samples. The average concentration of aluminum in the intact capsules was 296 ppm, and spectra were recorded at 18 wavelengths, although only one was needed for the analysis.

Figure 12:
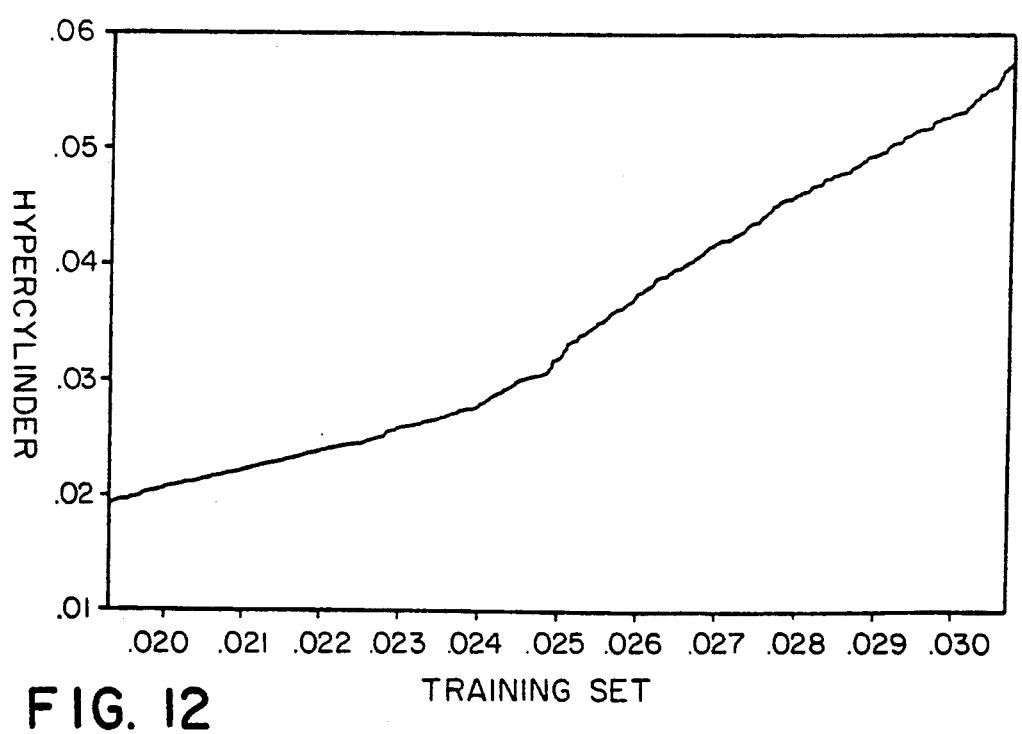

The hypothetical process-control problem in which floor sweepings were accidentally introduced into a batch of pharmaceutical capsules was also investigated with the present subcluster detection method. Eighteen-wavelength spectra from ten ANACIN-3 acetaminophen capsules containing an average of 221 ppm floor sweepings per capsule were used to produce the QQ plot in FIG. 12. The bend in the line indicates that the adulterated test set is a false-sample set with respect to the training set, i.e., the test set is not drawn from the same population as the training set. The upper line segment represents the test set, which is slightly larger in scale than the training set (as indicated by the slopes of the upper line segment and the best-fit line through the entire QQ plot, which was 2.5). The test set was larger than the training set because the floor sweepings were not evenly distributed throughout the 10-capsule set (homogeneity is difficult to achieve with floor sweepings and acetaminophen powder). The correlation coefficient calculated for this plot was 0.963, which makes the test set a false-sample set at the 98% confidence level of 0.966.

It will be appreciated that a simple student's t-test for the difference of the mean distance of the training set samples from their center and the mean distance of the test samples from the training set center does not perform as well as the present subcluster-detection procedure using QQ plots. For the floor-sweepings data, a t-test generated an 11% probability that the two mean distances were the same, i.e., that the test set was drawn from the same population as the training set. The t-test assumes that each set represents samples drawn from two normally distributed populations that have the same variance. When either assumption is violated, the t-test loses some of its power to differentiate between the sets. The present subcluster-detection method using QQ plots makes no assumptions about the shapes or sizes of either set, and consequently retains its power to differentiate between sets under a wider variety of circumstances.

False-sample spectra can be detected inside the 3 SD limit on a training-set spectral cluster when multiple test samples are available by using the present invention. Small differences between a training set and a test set (sub-cluster-detection) are reliably detected, even in cases where the distance between the centers of the sets is zero. Factors like instrumental drift and trace contamination that can generate errors too small to be noticeable in individual samples are large enough to show up clearly in a sample set using the present method. Thus, analyses can be carried out successfully for constituents present in samples at low concentrations (a few hundred ppm), and with simple process sensors using only a small number of wavelengths (even only 1 or 2). The present subcluster-detection method provides a solution to the false-sample problem in both quantitative analysis, where it can assign a group of samples to a particular prediction equation if a training set corresponding to that group of samples is available, and warn users if no such training set exists, and qualitative analysis, where false-sample detection is necessary in cases such as library searching and "smart calibration" (where the computer selects a prediction equation by a library search).

LIST OF SYMBOLS

Special defined operations:

| | |
|---|---|
| r | random number on $0 < x < 1$; |
| [x] | the greatest-integer function of a scalar, matrix, or array |
| $\partial(x)$ | ordered elements of x (x is a matrix or array) |
| = | equals, or "is replaced by" when the same variable appears on both sides of = |

Scalars:

| | |
|---|---|
| n | the training-set, test-set, and validation-set size, i.e., the number of samples that the set contains |
| d | the dimensionality of the analytical space |
| m | the number of sample-set replications forming a bootstrap distribution (user-determined) |
| i | an index for counting rows in a matrix or array |
| j | an index of counting columns in a matrix or array |
| $n_h$ | the number of bootstrap replicate spectral points falling inside a hypercylinder |
| p | proportion of a distance distribution to trim from each end of the distribution |

Matrices, vectors, and arrays:

| | |
|---|---|
| $B = (b_{ij})_{m,d}$ | m-by-d bootstrap distribution of training-set sample spectra |
| $B_{(X)} = (b_{ij})_{m,d}$ | bootstrap distribution of test-set sample spectra |
| $B_{(V)} = (b_{ij})_{m,d}$ | bootstrap distribution of validation-set sample spectra |
| $C = (c_j)_d$ | center of the bootstrap distribution B |
| $P = (p_{ij})_{m,n}$ | training-set sample numbers selected for the bootstrap-sample sets used to calculate bootstrap distributions |
| $T = (t_{ij})_{n,d}$ | training-set sample spectra |
| $X = (x_{ij})_{n,d}$ | test-set sample spectra |
| $V = (v_{ij})_{n,d}$ | validation-set sample spectra |
| $K = (k_j)_n$ | training-set sample numbers selected for a particular bootstrap sample |
| $B_{(s)} = (b_{(s)ij})_{n,d}$ | bootstrap sample set used to calculate single rows of a bootstrap distribution (B, $B_{(X)}$, or $B_{(V)}$) |
| $S_{(T)} = (s_{(T)i})_m$ | Euclidean distances of training-set replicates from C, the center of the bootstrap distribution of the training set |
| $S_{(X)} = (s_{(X)i})_m$ | Euclidean distances of test-set replicates from C |
| $S_{(V)} = (s_{(V)i})_m$ | Euclidean distances of validation-set replicates from C |
| $P_{(T)} = (p_i)_{m-2pm}$ | set of (m-2pm) indices used for trimming distance distributions |
| $C_{(T)} = (c_{(t)i})_{2m-4pm}$ | cumulative distribution function (CDF) formed by the trimmed and ordered elements of the training set bootstrap distribution; CDF has (2m-4pm) elements |
| $C_{(X)} = (c_{(x)i})_{2m-4pm}$ | CDF formed by the trimmed and ordered elements of the test-set and training-set bootstrap distributions |
| $C_{(V)} = (c_{(v)i})_{2m-4pm}$ | CDF formed by the trimmed and ordered elements of the valida- |

-continued

LIST OF SYMBOLS tion set and training-set bootstrap distributions

The invention has been described by way of a description and drawings that are intended in all senses to be illustrative and not restrictive. One of ordinary skill in the art will recognize that various modifications may be made without departing from the spirit or scope of the invention that is to be delimited only by the following claims.

What is claimed is:

1. A method for detecting nonhomogeneous samples comprising the steps of:
    assembling a first plurality of known samples to provide a training set of known samples;
    sequentially placing each of the training set of known samples in a spectroscopic apparatus for measuring a property of the sample as a function of an observable parameter;
    measuring the property of the known samples to obtain a training set of spectra at a second plurality of values of the observable parameters;
    storing said training set of spectra;
    forming a first bootstrap distribution from the training set;
    measuring the property of a third plurality of test samples at the second plurality of values of the observable parameters to obtain a set of test spectra;
    storing said set of test spectra;
    forming a second bootstrap distribution from the test set;
    forming first and second univariate distributions from the first and second bootstrap distributions;
    calculating a quantile-quantile relationship of the training and test sets; and
    determining whether the test set was drawn from a population substantially identical to the population from which the training set was drawn based on the quantile-quantile relationship.

2. The method of claim 1, wherein the number of the first plurality of samples essentially equals the number of the third plurality of samples.

3. The method of claim 1, further comprising the steps of collecting a validation set of spectra of a plurality of samples from the population from which the training set was collected, forming a third bootstrap distribution from the validation set, forming a third univariate distribution from the third bootstrap distribution, calculating a quantile-quantile relationship of the training and validation sets, and validating the training set based on the quantile-quantile relationship of the training and validation sets.

4. The method of claim 1 wherein the determining step includes calculating a correlation coefficient from the quantile-quantile relationship.

5. The method of claim 1, wherein the spectroscopic apparatus is a spectrometer, and the observable parameter is wavelength.

6. The method of claim 5, wherein the spectrometer is a near-infrared spectrometer.

7. The method of claim 1, wherein the spectroscopic apparatus is a mass spectrometer, and the observable parameter is mass.

8. A method for detecting nonhomogeneous samples of pharmaceutical capsules comprising the steps of:
    assembling a first plurality of known samples from a population of pharmaceutical capsules to provide a training set of known samples;
    sequentially placing each of the training set of known samples in a spectroscopic apparatus for measuring a property of the sample as a function of an observable parameter;
    measuring the property of the known samples to obtain a training set of spectra at a second plurality of values of the observable parameters;
    storing the training set of spectra;
    forming a first bootstrap distribution from the training set;
    obtaining a test set of spectra at the second plurality of values of the observable parameters from a third plurality of samples of pharmaceutical capsules;
    forming a second bootstrap distribution from the test set;
    forming first and second univariate distributions from the first and second bootstrap distributions;
    calculating a quantile-quantile relationship of the training and test sets; and
    determining whether the test set was drawn from a population substantially identical to the population from which the training set was drawn based on the quantile-quantile relationship.

9. The method of claim 8, wherein the determining step includes calculating a correlation coefficient from the quantile-quantile relationship.

10. The method of claim 9, further comprising the steps of collecting a validation set of spectra of a plurality of samples from the population from which the training set was collected, forming a third bootstrap distribution from the validation set, forming a third univariate distribution from the third bootstrap distribution, calculating a quantile-quantile relationship of the training and validation sets, and validating the training set based on the quantile-quantile relationship of the training and validation sets.

11. The method of claim 8, wherein the spectroscopic apparatus is a spectrometer, and the observable parameter is wavelength.

12. The method of claim 11, wherein the spectrometer is a near-infrared spectrometer.

13. The method of claim 8, wherein the spectroscopic apparatus is a mass spectrometer, and the observable parameter is mass.

* * * * *